United States Patent
Desprez

(10) Patent No.: US 7,816,112 B2
(45) Date of Patent: Oct. 19, 2010

(54) CASTABLE DIFFUSION MEMBRANE FOR ENZYME-BASED SENSOR APPLICATION

(75) Inventor: Valerie Desprez, Heidelberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 401 days.

(21) Appl. No.: 10/886,802

(22) Filed: Jul. 7, 2004

(65) Prior Publication Data
US 2005/0009130 A1    Jan. 13, 2005

(30) Foreign Application Priority Data
Jul. 11, 2003    (EP) ................... 03015882

(51) Int. Cl.
*C12N 9/14*    (2006.01)
(52) U.S. Cl. .................. 435/195; 435/7.1; 435/15; 435/287.1
(58) Field of Classification Search .............. None
See application file for complete search history.

(56) References Cited

U.S. PATENT DOCUMENTS

| | | | |
|---|---|---|---|
| 4,409,339 A * | 10/1983 | Matsuda et al. | 521/143 |
| 4,900,933 A | 2/1990 | Nestor et al. | |
| 5,124,128 A | 6/1992 | Hildenbrand et al. | |
| 5,422,246 A | 6/1995 | Koopal et al. | |
| 5,633,081 A | 5/1997 | Clough et al. | |
| 6,107,083 A | 8/2000 | Collins et al. | 435/288.7 |
| 6,156,550 A | 12/2000 | Glad | |
| 6,214,185 B1 | 4/2001 | Offenbacher et al. | 204/403 |

FOREIGN PATENT DOCUMENTS

| | | |
|---|---|---|
| EP | 0 175 195 A2 | 8/2005 |
| WO | WO 99/30152 | 6/1999 |
| WO | WO 01/69222 A2 | 9/2001 |

OTHER PUBLICATIONS

Hikuma et al. (Analytica Chimica Acta, vol. 306, pp. 209-215, 1995).*

* cited by examiner

*Primary Examiner*—Hope A Robinson
(74) *Attorney, Agent, or Firm*—Dinsmore & Shohl LLP

(57) ABSTRACT

The invention relates to a diffusion membrane for an enzyme-based sensor, a sensor comprising the diffusion membrane as well as the use of the enzyme-based sensor for the detection and/or determination of a substance, in particular an enzyme substrate, e.g., glucose.

6 Claims, No Drawings

CASTABLE DIFFUSION MEMBRANE FOR ENZYME-BASED SENSOR APPLICATION

BACKGROUND OF THE INVENTION

The present invention relates to a diffusion membrane for an enzyme-based sensor, a sensor comprising the diffusion membrane as well as a method of producing the enzyme-based sensor and the use of the enzyme-based sensor for the detection and/or determination of a substance, in particular an enzyme substrate, e.g., glucose.

Enzyme-based sensors are widely used to determine substances of interest in a qualitative as well as a quantitative manner in the blood and in other body liquids. Enzyme-based sensors are in particular used for the determination of enzyme substrates. In an enzyme-based sensor a so-called sensing reaction (sometimes also referred to in the art as a "transducer reaction") occurs wherein a substance is converted under participation of at least one enzyme into another substance, which can be detected directly or indirectly. An example of such a sensing reaction is the enzyme catalyzed oxidation of glucose. Usually, this reaction uses oxygen as an electron acceptor. In the course of the reaction, glucose is converted into gluconolactone and the oxygen is converted into hydrogen peroxide. A sensing reaction either could measure the consumption of glucose and oxygen or the production of hydrogen peroxide or gluconolactone.

An enzyme-based sensor usually comprises several layers, among them an enzyme layer and a cover membrane or outer layer. This cover membrane is directly in contact with the sample and limits the diffusion of the substances necessary for the sensing reaction, especially the enzyme substrate or cosubstrate.

Enzyme-based sensors can be provided as electrochemical sensors or as optical sensors (optodes). The construction and function of a glucose optode is for example described in U.S. Pat. No. 6,107,083. The construction and function of an electrochemical glucose sensor is for example described in International Publication No. WO 99/30152.

Particularly, enzyme-based sensors which are used for the determination of glucose, lactate or creatinine are typically constructed with oxidoreductases and the detection is based on the oxygen consumption. In this case, the sensor comprises a cover membrane being a porous or at least a permeable polymer membrane, which controls the permeation of both the enzyme substrate and oxygen.

The currently available diffusion membranes for enzyme-based sensor application suffer from various disadvantages. According to one approach known in the state of the art, cover membranes for enzyme-based sensor applications are preformed membranes consisting of microporous structures from non-hydrating polymers like polycarbonate, polypropylene and polyesters. The porosity of such membranes is provided by physical means, e.g., by neutron or argon track etching. Glucose and oxygen permeate across such membranes predominantly in these pores filled with blood or other body liquids. One major disadvantage is that such membranes are preformed and not castable. A preformed membrane has to be attached to the enzyme layer. Very often the membranes are mechanically attached to the enzyme layer. Such mechanical attachments are expensive and technically complex. Further problems occur insofar as it is difficult to apply the membrane onto the underlying layer without producing air bubbles. Similar problems also occur when the membrane is for example glued onto an underlying layer.

Another approach known in the state of the art are castable cover membranes. Such cover membranes are generally formed by applying a solution of a polymer to an enzyme layer and by evaporating the solvent. Such membranes consist of polymer structures with hydrophilic and hydrophobic regions. Upon exposure to water, the hydrophilic region of the membranes absorb water, thus providing in the swelled structure a permeation path, e.g., for glucose. However, those membranes provide no defined porosity. In this approach the polymer itself has to provide the permeation, therefore not all polymers are suitable and thus the election of polymers is limited.

One disadvantage is that polymers, which are suitable for the use of castable membranes, are very often soluble only in aggressive or toxic solvents. Examples for this are cellulose acetate, which is soluble in DMSO and acetone, and PVC, which is soluble in tetrahydrofurane and cyclohexanone. This circumstance is relevant not only for safety reasons but also because the enzymes present in the enzyme layer may be destroyed by these solvents. Moreover, the effectiveness of such a membrane depends upon the dispersion of the hydrophilic domains within the hydrophobic matrix. Since it is difficult to achieve a homogenous dispersion in and during the production process of the membrane, the consequence is an inhomogeneous distribution of the hydrophilic domains. This results for example in a poor reproducibility.

Offenbacher et al. (U.S. Pat. No. 6,214,185 B1) describe a cover membrane with better coating reproducibility. The membrane is made of a PVC copolymer which allows a quite satisfying adjustment of the permeability due to the presence of a hydrophilic copolymer component. However, such a PVC cover membrane shows limitations for multiple measurements when used for a sensor based on the consumption of oxygen since the regeneration of the oxygen reservoir of the sensor is very slow.

SUMMARY OF THE INVENTION

It is against the above background that the present invention provides certain unobvious advantages and advancements over the prior art. In particular, the inventor has recognized a need for improvements in diffusion membranes for enzyme-based sensor applications.

Although the present invention is not limited to specific advantages or functionality, it is noted that the castable membrane has good processability and provides a defined permeability, which can also be used for multiple measurements.

In accordance with one embodiment of the present invention, a diffusion membrane for an enzyme-based sensor application is provided, wherein the membrane comprises at least one polymer material and pore-maker particles dispersed in the at least one polymer material.

The membrane according to the present invention comprises pore-maker particles dispersed in one or more polymer materials. The porosity of the membrane is provided by the pore-maker particles. Thus, from the permeability or porosity point of view there is no limitation when electing the polymer.

The polymer material used for the diffusion membrane of the present invention can generally be any castable polymer material or a mixture of polymer materials. According to the planned application, for example, non-toxic or easily applicable materials can be used.

Typical polymer materials can be selected from non-water soluble polymers and typically from polyurethane, polyacrylamide, polystyrene, polyvinyl esters and co-polymers of, e.g., butadiene and styrene.

Due to the various election possibilities with regard to the polymer material, a castable diffusion membrane can be provided easily, which can be coated directly in a reproducible manner. The diffusion membrane can for example be coated on an underlying layer, typically onto an enzyme layer. It is an advantage of the diffusion membrane of the present invention that directly coating the diffusion membrane onto the enzyme layer does not alter the related enzyme activity. Furthermore, a diffusion membrane can easily be provided, which is insoluble in body liquids such as, for example, blood.

The diffusion membrane according to the present invention can comprise pore-maker particles dispersed in the layer forming polymer material. The pore-maker particles provide the porosity of the membranes and thus the permeability. The particles used as pore-maker are typically stable particles or mixtures of such particles possessing inherent and defined porosity. The size of the pore-maker particles is typically between about 0.5 and about 100 µm and, more typically from about 1 to about 50 µm.

The membrane has a defined porosity, which is provided by pores, formed by the pore-maker particles according to the present invention. According to the application of the membrane, the size of the pores can be varied. The size of the pores is typically within the range of the size of the pore-maker particles.

The diffusion membrane according to the present invention comprises pore-maker particles in an amount that is typically between about 0.5 and about 70 weight %, more typically from about 0.7 to about 50 weight %, and most typically from about 1 to about 40 weight % based on the total weight of the dried membrane. If the proportion of the pore-maker particles exceeds a certain limit, then the membrane can become mechanically instable; if too little pore-maker particles are added then the membrane could become impermeable.

For the use as pore-maker particles in the membrane, essentially all stable particles and mixtures of such particles are useful, which particles possess an inherent and defined porosity. According to the desired application and/or pore size, suitable particles can be elected. Examples of suitable pore-maker particles include inorganic or organic particles made from Kieselguhr, silica gel, cellulose, precipitated gypsum, kaolin, glass or the like. The particles can be based on silicon dioxide and, more particularly, on diatomaceous earth. Typical diatomeous earth is sold under the tradename Celatom®.

The diffusion membrane according to the present invention can further comprise other elements such as, for example, carbon black for optical isolation, pigments like titanium dioxide for improved remission properties of the membrane, or wetting agents.

The thickness of the diffusion membrane according to the present invention can be chosen flexibly with regard to the desired use and/or permeation rate. Suitable thicknesses are within the range of about 0.5 to about 1000 µm, typically between about 3 and about 500 µm, and more typically between about 5 and about 100 µm.

The permeation of the diffusion membrane can thus be easily adjusted by varying the coating thickness and/or the concentration of the pore-maker particles.

In one embodiment of the diffusion membrane according to the present invention, the size of the pore-maker particles corresponds at least to the thickness of the layer of the diffusion membrane, the relation between the particle size and the layer thickness is approximately 1:1 or $\geq$1:1. In this embodiment, the size of the pore-maker particles is chosen in a way that the single particles or clusters of single particles form continuous pores from the surface of the sensor to the enzyme layer. Thus, a diffusion of the substances is provided.

In accordance with another embodiment of the present invention, an enzyme-based sensor comprising a diffusion membrane as described above is provided. The sensor comprises several layers, wherefrom at least one layer is an enzyme layer. The enzyme-based sensor of the present invention can further comprise a cover layer and at least one underlying layer. Depending on the type of the sensor, further layers can for example be an interference-blocking layer, a layer for optical isolation, an electro-conductive layer, an indicator layer or a base electrode.

Since the permeability of the diffusion membrane can be adjusted as desired, the diffusion membrane provides a fast regeneration of the sensor. In the case of a sensing reaction based for example on the consumption of oxygen, the oxygen permeation can be adjusted in such a manner that the sensor regeneration, e.g., the regeneration of the oxygen reservoir, is very fast. Thus, the sensor of the present invention can also be used for multiple measurements.

The enzyme layer of the enzyme-based sensor can for example comprise oxidative enzymes such as, for example, glucose oxidase, cholesterol oxidase or lactate oxidase. The enzyme layer may also comprise an enzyme mixture such as, for example, an enzyme cascade, which makes possible the detection of analytes which cannot be directly detected such as, for example, the creatine. Creatine cannot be enzymatically oxidized by a simple enzyme but requires several enzymatic steps to generate an analyte derivative, which is detectable by optical or amperometric means. A suitable enzyme cascade system for the detection and/or determination of creatinine can comprise, e.g., creatinine amidohydrase, creatinine amidohydrolase, and sarcosine oxidase.

In the sensor according to the present invention, the diffusion membrane is typically deposited as cover layer. In this case, after solvent evaporation of the dispersion a stable cover layer is formed. The diffusion membrane is further typically coated directly on an underlying layer, typically an enzyme layer. By a direct coating of the membrane, favorably, the membrane layer is attached to the underlying layer by physical adhesion without a mechanical fixation and/or the use of glue.

When the diffusion membrane is used as cover layer, it is directly in contact with the test sample and regulates the diffusion of the substances necessary for the sensing reaction, typically the substrates or cosubstrates. The diffusion membrane according to the present invention thus provides the sensor with a controlled permeability.

The enzyme-based sensor of the present invention can represent any kind of a biosensor. Examples of suitable biosensors are for example optical sensors. With typical optical sensors, the consumption of oxygen due to an enzymatic reaction can be detected using an appropriate dye which is sensitive to oxygen, e.g., a luminescent dye quenchable with oxygen. Furthermore, an electrochemical sensor is suitable for use in accordance with the present invention.

Especially in connection with sensors which use oxygen consumption as a means for analyte determination, the membranes according to this invention show big advantages. The pores created by the pore-maker particles allow for the adjustment of diffusion of the analyte molecules, e.g., glucose, across the membrane, and the choice of the polymer influences the permeability of oxygen. Although oxygen permeation across the membrane in part is also possible through the pores created by the pore-maker particles, it essentially is influenced by the polymer layer, especially if this has a high oxygen permeability.

In accordance with yet another embodiment of the present invention, the use of an enzyme-based sensor as described above for the detection or quantitative determination of a substance, typically an enzyme substrate, is provided.

In the field of medicine, a possibility of the use is for example the determination of physiological parameters. A determination and/or detection can be carried out in any liquid, for example in various body liquids such as blood, serum, plasma, urine, and the like. A typical use of the sensor is a detection and/or determination of analytes in blood.

A possible use of the sensors according to the present invention is for example the determination of blood glucose in patients suffering from diabetes. Other metabolic products that can be determined with the enzyme-based sensor according to the present invention are for example cholesterol or urea.

Another possible use of the enzyme-based sensor of the present invention is in the field of environmental analytics, process control in biotechnology, and food control.

With the use according to the present invention of the enzyme-based sensor, a wide variety of substances, for example, enzyme substrates and/or cosubstrates, can be determined and/or detected. Suitable enzyme substrates are for example cholesterol, sucrose, glutamate, ethanol, ascorbic acid, fructose, pyruvat, ammonium, nitrite, nitrate, phenol, NADH, glucose, lactate or creatinine. Typically, a determination and/or detection of glucose, lactate or creatinine is performed. A typical substance to be detected and/or determined is glucose.

Since the regeneration of the enzyme-based sensor can be influenced by adjusting the permeation, the regeneration is fast enough to allow multiple measurements. In a typical use of the sensor multiple measurements are performed. Further, the enzyme-based sensor can be employed for every sensor-application known in the art such as, for example, for a single use application or as a permanent sensor for multi use applications.

In accordance with still another embodiment of the present invention, a method of producing an enzyme-based sensor as described above is provided. This method comprises forming a dispersion comprising at least one polymer material and pore-maker particles, and casting the dispersion directly on an underlying layer to form a diffusion membrane. The method can optionally further comprise drying the dispersion.

The method according to the present invention allows a direct casting of the membrane due to the broad option of polymer materials. By using suitable polymer materials, it is furthermore possible to work without solvents, if desired. Further, the materials can be elected in a way that a heating of the dispersion is not necessary. Thus, by the method according to the present invention, an easy handling is provided.

The method allows the application of the membrane without damaging lower layers, e.g., the enzyme layer. The membrane can for example be applied directly onto the enzyme layer without influencing the enzymes. In one embodiment, the dispersion is casted directly on an enzyme layer.

In the method according to one embodiment of the present invention, the dispersion is typically attached to the underlying layer by physical adhesion. Thus, a mechanical attachment of the membrane including the above mentioned disadvantages is not necessary.

If desired, the dispersion can be dried after the application on the underlying layer. Essentially, every drying method known in the technical field can be used.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

DETAILED DESCRIPTION OF THE INVENTION

In order that the invention may be more readily understood, reference is made to the following examples, which are intended to illustrate the invention, but not to limit the scope thereof.

EXAMPLE 1

Membrane for the determination of the glucose concentration in liquid samples.

For the preparation of the membrane dispersion, the following components were mixed:

TABLE 1

| | |
|---|---|
| Polyurethane dispersion (20% in ethanol) (Tyndale Plains-Hunter, Ltd.) | 2 g |
| Celatome MW 27 (Eagle-Picher Minerals, Inc.) | 0.2 g |
| optionally Carbon black | 0.06 g |

The mixture was applied on top of the enzyme layer of an OptiCCA single use glucose sensor (Roche Diagnostics Corp.) in a 20 μm thick layer. After drying at room temperature, a sensor spot (4 mm diameter) overcoated with the membrane of the invention was cut from the sensor foil and placed in a flow through cell of which the channel was filled with an appropriate buffer before injecting the sample.

Raw intensities produced by the luminescence quenching of the luminescent dye contained in the oxygen sensitive layer were then measured. The following kinetic measurements (fluorescence intensity change: Äl per second) were obtained with three different glucose control solutions tonometered at 150 Torr oxygen partial pressure.

TABLE 2

| Glucose concentration (mg/dL) | Relative slope (Äl per second) |
|---|---|
| 50 | 565 |
| 113 | 3972 |
| 356 | 28796 |

EXAMPLE 2

Example 2 shows the fast sensor regenerations and the possibility of multiple measurements (3 measurements with the control solution containing 356 mg/dL glucose and 150 Torr oxygen partial pressure). The sensor used in Example 2 was prepared according to Example 1, but was not completely identical to the sensor of Example 1 due to handcoating of the membrane.

TABLE 3

| No. of measurements | Relative slope (Äl per second) | Regeneration time (seconds) |
|---|---|---|
| 1 | 34439 | <60 |
| 2 | 36906 | <60 |
| 3 | 35760 | <60 |
| CV % | 3.5 | |

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A diffusion membrane for an enzyme-based sensor application, wherein the membrane comprises:
    at least one castable polymer material; and
    porous pore-maker particles dispersed in the at least one castable polymer material, the porous pore-maker particles having a size of about 0.5 µm to about 100 µm.

2. The diffusion membrane of claim 1, wherein the porous pore-maker particles are present in an amount of about 0.5% to about 70% by weight.

3. The diffusion membrane of claim 1, wherein the porous pore-maker particles comprise diatomaceous earth.

4. The diffusion membrane of claim 1, wherein the thickness of the membrane is about 0.5 µm to about 1000 µm.

5. The diffusion membrane of claim 1, wherein the at least one castable polymer material is selected from the group consisting of polyurethane, polyacrylamide, polystyrene, polyvinyl esters, copolymers of butadiene and styrene, and mixtures thereof.

6. The diffusion membrane of claim 1, wherein the porous pore-marker particles comprise inorganic or organic particles selected from the group consisting of Kieselguhr, silica gel, cellulose, precipitated gypsum, kaolin, glass, silicon dioxide, and mixtures thereof.

* * * * *